(12) United States Patent
Khan et al.

(10) Patent No.: US 11,479,482 B1
(45) Date of Patent: Oct. 25, 2022

(54) HYDROGEN-BONDED ORGANIC FRAMEWORK (HOF) FOR WATER UPTAKE

(71) Applicant: KING FAHD UNIVERSITY OF PETROLEUM AND MINERALS, Dhahran (SA)

(72) Inventors: Mohd Yusuf Khan, Dhahran (SA); Abuzar Khan, Dhahran (SA); Aasif Helal, Dhahran (SA); Zain H. Yamani, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 17/828,591

(22) Filed: May 31, 2022

(51) Int. Cl.
| | | |
|---|---|---|
| *C02F 1/28* | (2006.01) | |
| *B01J 20/22* | (2006.01) | |
| *C07C 63/307* | (2006.01) | |
| *C07D 249/14* | (2006.01) | |

(52) U.S. Cl.
CPC ............... *C02F 1/285* (2013.01); *B01J 20/22* (2013.01); *C07C 63/307* (2013.01); *C07D 249/14* (2013.01); *C07B 2200/13* (2013.01)

(58) Field of Classification Search
CPC ...... C07C 63/307; C07D 249/14; C02F 1/285
See application file for complete search history.

(56) References Cited

U.S. PATENT DOCUMENTS

| | | | |
|---|---|---|---|
| 9,718,748 B1 | 8/2017 | Allendorf et al. | |
| 11,078,219 B2 | 8/2021 | Ohashi | |
| 2020/0129970 A1* | 4/2020 | Li | ................... C07C 51/418 |

FOREIGN PATENT DOCUMENTS

| | | |
|---|---|---|
| CN | 109608655 B | 12/2020 |
| CN | 113045460 A | 6/2021 |
| CN | 109642094 B | 9/2021 |
| CN | 113499469 A | 10/2021 |
| ES | 2 815 650 T3 | 3/2021 |

OTHER PUBLICATIONS

Cui (Journal of Molecular Structure; 2015, 1081, 182-186).*
Ilango Aswin Kumar, et al., "Fabrication of lanthanum linked trimesic acid as porous metal organic frameworks for effective nitrate and phosphate adsorption", Journal of Solid State Chemistry, vol. 302, Oct. 2021, 4 pages (Abstract only).
Biao-Biao Hao, et al., "Two Hydrogen-Bonded Organic Frameworks with Imidazole Encapsulation: Synthesis and Proton Conductivity", Crystal Growth & Design, vol. 21, Issue 7, Jun. 4, 2021, pp. 3908-3915 (Abstract only).
Kaikai MA, et al., "Ultrastable Mesoporous Hydrogen-Bonded Organic Framework-Based Fiber Composites toward Mustard Gas Detoxification", Cell Reports, Physical Science, vol. 1, Feb. 26, 2020, pp. 1-12.

* cited by examiner

*Primary Examiner* — Pancham Bakshi
(74) *Attorney, Agent, or Firm* — Oblon, McClelland, Maier & Neustadt, L.L.P.

(57) ABSTRACT

A method of water uptake is provided. The method includes contacting a hydrogen-bonded organic framework (HOF) with water to form a mixture where the HOF comprises hydrogen bonded units of trimesic acid and guanazole. The HOF has a sheet structure, where the sheets form an intercrossed macroporous network with pores on a surface. The HOF absorbs at least a portion of the water in the mixture.

18 Claims, 15 Drawing Sheets

HYDROGEN-BONDED ORGANIC FRAMEWORK (HOF) FOR WATER UPTAKE

BACKGROUND

TECHNICAL FIELD

The present disclosure is directed to a HOF, particularly a HOF for water uptake.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Water is a vital substance for sustaining life, and approximately 71% of the earth's surface is covered with water. More than 65% of the world's total population is facing water shortages even though an abundance of water exists in the atmosphere in the form of water vapor, clouds, and fog. Conventional methods of capturing atmospheric water, such as dewing from damp air and fog, require 100% relative humidity (RH) or a large amount of energy, and thus, are not viable solutions in most environments.

Recent advancements in the design of porous materials for these applications have moved next-generation water sorbents closer to applicability, but methods to precisely control the hydrophilicity of a sorbent are still needed. In recent years, metal-organic frameworks (MOFs) have emerged as a potential candidate in utilization for water uptake or capture. MOFs provide an ideal platform for interrogating the hydrogen bonding structure of confined water due to their modular nature allowing for tuning of the metal ion, and hydrophilicity without altering the overall framework topology. Although MOFs have been developed in the past, a framework still needs to be created with improved water uptake and excellent stability.

Hydrogen-bonded organic frameworks (HOFs) are a new class of crystalline, porous materials that are assembled from small organic molecules. Generally, HOFs display a high level of crystallinity, solution processability, simple healing and purification due to reversible and varying features of hydrogen-bonding (H-bonding) interconnections. These exceptional features of HOFs provide a diverse platform to explore a variety of multifunctional porous materials. However, HOFs have not yet been investigated for the application of water uptake, despite the presence of H-bonding within the framework.

In light of aforementioned drawbacks, it is one object of the present disclosure to provide a HOF with water uptake capacity.

SUMMARY

In an exemplary embodiment, a method of water uptake is described. The method includes contacting a hydrogen-bonded organic framework (HOF) with water to form a mixture, where the HOF includes hydrogen bonded units of trimesic acid and guanazole. The HOF has a sheet structure, where the sheets form an intercrossed macroporous network with pores on a surface. The HOF absorbs at least a portion of the water in the mixture.

In some embodiments, the molar ratio of trimesic acid to guanazole in the HOF is 1-5 to 1-5.

In some embodiments, the molar ratio of trimesic acid to guanazole in the HOF is 1 to 1.

In some embodiments, the HOF is substantially crystalline.

In some embodiments, the sheets of the HOF have a thickness of 1-15 nanometers (nm).

In some embodiments, the pores of HOF have a diameter of 100-1,000 nm.

In some embodiments, the HOF is stable up to 280° C.

In some embodiments, the method further includes grinding the HOF into a powder and drying at a temperature of 50-80° C. prior to contact with water.

In some embodiments, the method includes heating the mixture to a temperature of 50-100° C.

In some embodiments, the weight ratio of HOF to water in the mixture is 1 to 100-1,000.

In some embodiments, the HOF has a maximum water uptake capacity of 650 mL per gram of HOF.

In some embodiments, the water includes at least one ion selected from the group consisting of calcium, bicarbonate, magnesium, sodium, potassium, chloride, nitrate, and sulfate.

In some embodiments, the intercrossed macroporous network structure of the HOF is maintained in the presence of at least one ion in the water.

In some embodiments, the method further includes separating the HOF from the mixture to leave a wet HOF and drying the wet HOF at a temperature of at least 60° C. for 12-24 hours to form a recycled HOF.

In some embodiments, the method includes recycling the HOF up to 10 times following the steps of water absorption and drying.

In some embodiments, the water absorption capacity of the HOF is maintained following recycling.

In some embodiments, the intercrossed macroporous network structure of the HOF is maintained following recycling.

In some embodiments, the HOF is made by a method including dissolving trimesic acid in water at a temperature of 50-80° C. to form a trimesic acid solution; and further dissolving guanazole in water to form a guanazole solution. The method further includes adding dropwise the guanazole solution to the trimesic acid solution at a temperature of 50-80° C. to form a reaction mixture; cooling the reaction mixture to 20-40° C. to form a precipitate; and further separating and drying the precipitate at a temperature of 50-80° C. to form the HOF.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
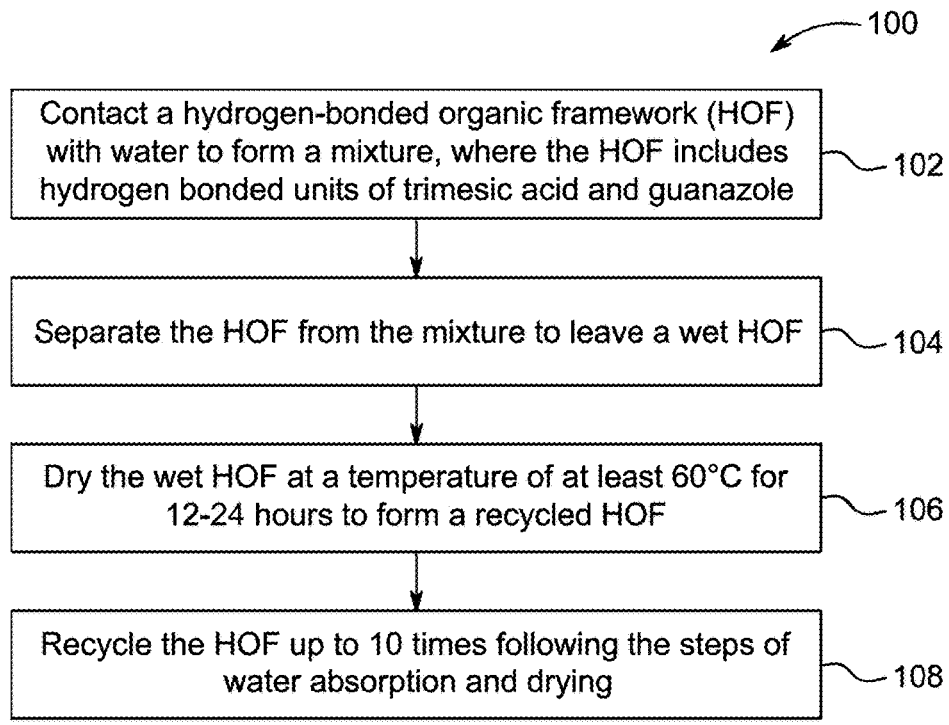
FIG. 1 is a flow chart of a method of water uptake, according to embodiments of the present disclosure.

The definitions of the terms as used herein are as follows. Unless specified otherwise, these terms are used alone or in combination with another term in the meaning as defined.

The term "organic linker" means a chemical compound having a chemical structure substituted with (a) at least one functional group, wherein the said functional group is capable of promoting hydrogen bond(s) with at least one other organic linker.

The term "hydrogen bond" means a bond that results from an attractive interaction between a hydrogen atom and an electronegative atom, wherein the hydrogen atom itself is covalently attached to another electronegative atom, for example, but not limited to, oxygen (O), nitrogen (N), chlorine (Cl), fluorine (F), etc.

The term "hydrogen-bonded organic framework" or "HOF" is defined as a material assembled from organic linker molecules through intermolecular hydrogen bonding.

The term "one-pot" reaction or method is defined as a process where a compound is subjected to one or more reactions or interactions in a single vessel. In the case of the current disclosure, the compound is trimesic acid, which interacts with guanazole to form the HOF in a single vessel.

The term "carboxylic acids" or "carboxylic acid compounds" includes aliphatic, cyclic, aromatic, non-aromatic, carbocyclic, heterocyclic, aromatic carbocyclic, non-aromatic carbocyclic, aromatic heterocyclic, or non-aromatic heterocyclic hydrocarbons that are substituted with (a) at least one functional group of formula —COOH, or (b) at least one moiety having at least one functional group of formula —COOH. Non-limiting examples of di-carboxylic acids include benzoic acid, 3-carboxy-1,2,4-triazole, 5-carboxy-1,2,4-triazole, 4-carboxy-1,2,3-triazole, 5-carboxy-1,2,3-triazole, 5-carboxytetrazole, 2-carboxy-1,3,5-triazine, 3-carboxy-1,2,4-triazine, 5-carboxy-1,2,4-triazine, 6-carboxy-1,2,4-triazine, and like.

The term "amines", "amine compounds", or "amine substituted compounds" includes aliphatic, cyclic, aromatic, non-aromatic, carbocyclic, heterocyclic, aromatic carbocyclic, non- aromatic carbocyclic, aromatic heterocyclic, or non-aromatic heterocyclic hydrocarbons that are substituted with (a) at least one functional group of formula —NRaRb, or (b) at least one moiety having at least one functional group of formula —NRaRb, wherein Ra and Rb are each independently hydrogen, alkyl, aryl, heterocyclyl, or any other substituent. Non-limiting examples of amines include aminobenzene, 3-amino-1,2,4-triazole, 5-amino-1,2,4-triazole, 4-amino-1,2,3-triazole, 5-amino-1,2,3-triazole, 5-aminotetrazole, 2-amino-1,3,5-triazine, 3-amino-1,2,4-triazine, 5-amino-1,2,4-triazine, 6-amino-1,2,4-triazine, and like.

The term "hygroscopic" is defined as the phenomenon of attracting and holding water molecules via either absorption or adsorption from the surrounding environment.

The term "dessicant" is defined as a hygroscopic substance that is used to induce or sustain a state of dryness (desiccation) in its vicinity.

The term "organic solvent" refers to carbon-based substances capable of dissolving or dispersing one or more other substances, which includes but is not limited to acetone, acetonitrile, ethanol, formaldehyde, ether, ethyl acetate, hexane, toluene, xylenes, methylene chloride, and chloroform.

In the drawings, like reference numerals designate identical or corresponding parts throughout the several views. As used herein, the words "a," "an" and the like generally carry a meaning of "one or more," unless stated otherwise. Further, the terms "approximately," "approximate," "about," and similar terms generally refer to ranges that include the identified value within a margin of 25%, 20%, 10%, or 5%, and any values therebetween. Furthermore, the terms "equal to," "substantially equal to," and similar terms generally refer to ranges that include the identified value within a margin of 75%, 80%, 85%, 90%, 95%, or 100%, and any values therebetween.

Aspects of the present disclosure are directed to a 2D-hydrogen-bonded organic Framework (HOF) produced by a green and simple "one-pot" synthetic approach, with trimesic acid and guanazole. The resultant HOF, labeled throughout as KFUPM-HOF, is characterized by relevant analytical techniques for the structure and morphology. The KFUPM-HOF is examined for its water holding capacity with deionized (DI) and tap water. The obtained water uptake of the KFUPM-HOF is up to 600 times its weight.

The present disclosure also provides a method 100 of water uptake. Referring to FIG. 1A, a schematic flow diagram of a method of increasing the water uptake is illustrated. The order in which the method is described is not intended to be construed as a limitation, and any number of the described method steps can be combined in any order to implement the method.

Additionally, individual steps may be removed or skipped from the method without departing from the spirit and scope of the present disclosure.

At step 102, method 100 includes contacting a HOF with water to form a mixture. In an embodiment, the water may be but is not limited to de-ionized water, tap water, seawater, brackish water, sewage water, alkaline water (pH>7), and acidic water (pH<7). In an embodiment, metal ions in the water may include but are not limited to $Li^+$, $Na^+$, $K^+$, $Be^{2+}$, $Mn^{2+}$, $Fe^{2+}$, $Co^{2+}$, $Ni^{2+}$, $Cu^{2+}$, $Zn^{2+}$, $Cd^{2+}$, $SC^{3+}$, $Ti^{3+}$, $V^{3+}$, $Cr^{3+}$, $Fe^{3+}$, $Rh^{3+}$, $Ga^{3+}$, $In^{3+}$, $Ce^{4+}$, $Th^{4+}$, $Pa^{4+}$, $U^{4+}$, $Np^{4+}$, $Pu^{4+}$, $Mg^{2+}$, $Ca^{2+}$, $Sr^{2+}$, $Ba^{2+}$, $Al^{3+}$, $Y^{3+}$, $La^{3+}$, $Ag^+$, $Tl^+$, $Pb^{2+}$, $Ti^{3+}$, $Bi^{3+}$, $Sn^{2+}$, $Sn^{2+}$, and $Pd^{2+}$. In an embodiment, the water may include organic contaminants such as but not limited to dyes, humic substances, phenolic compounds, petroleum, surfactants, pesticides, and pharmaceuticals. In an embodiment, the water is DI water with a resistivity of 18-19 megohm. In an embodiment, the water is tap water, which is water obtained directly from a faucet or tap, that has not been purified, distilled, or otherwise treated. In an embodiment, the tap water includes at least one ion selected from the group consisting of calcium, bicarbonate, magnesium, sodium, potassium, chloride, nitrate, and sulfate. In an embodiment, the water is in liquid form and the HOF is at least partially submerged in the water, preferably 10% 20%, 30%, 40%, 50%, 60%, 70%, 80%, or 90% submerged. In an embodiment, the HOF is fully submerged in the water. In an embodiment, the HOF is contacted with atmospheric water, or water vapor. In an embodiment, the humidity in the ambient air is at least 10%, preferably 20%, 30%, 40%, 50%, 60%, 70%, 80%, 90%, or 100%.

In one aspect of the present disclosure, the HOF includes di- or tri-amine compounds as organic linkers to yield the HOF, wherein the di-amine compound is a compound substituted with two amine functional groups and the tri-amine compound is a compound substituted with three amine functional groups. The di- or tri-amines utilized may be di- or tri-amine-substituted acyclic or cyclic compounds. Any type of acyclic compounds is contemplated herein, for example, but not limited to, open-chain, straight-chain, or branched-chain compounds. The said compounds may be saturated or unsaturated acyclic compounds. Further, any type of cyclic compounds is contemplated herein, comprising one or more rings. The cyclic compounds may be 3-, 4-, 5-, 6-, 7-, 8-, or 9-membered ring compounds of any type, for example, but not limited to, non-aromatic carbocyclic, aromatic carbocyclic, non-aromatic heterocyclic, or aromatic heterocyclic ring compounds. The said rings may be fused/condensed rings of any of the aforementioned type, or a combination thereof. In an embodiment, the HOF includes guanazole, melamine, or p-phenylenediamine. In an embodiment, the HOF includes guanazole.

In another aspect of the present disclosure, the HOF includes di- or tri-carboxylic acid compounds as organic linkers to yield the HOF, wherein the di-carboxylic acid compound is a compound substituted with two carboxylic acid functional groups and the tri-carboxylic acid compound is a compound substituted with three carboxylic acid functional groups. The di- or tri-carboxylic acids utilized may be di- or tri-carboxylic acid substituted acyclic or cyclic compounds. Any type of acyclic compounds is contemplated herein, for example, but not limited to, open-chain, straight-chain, or branched-chain compounds. The said compounds may be saturated or unsaturated acyclic compounds. Further, any type of cyclic compounds is contemplated herein comprising one or more rings. The cyclic compounds may be 3-, 4-, 5-, 6-, 7-, 8-, or 9-membered ring compounds of any type, for example, but not limited to, non-aromatic carbocyclic, aromatic carbocyclic, non-aromatic heterocyclic, or aromatic heterocyclic ring compounds. The said rings may be fused/condensed rings of any of the aforementioned type, or a combination thereof. In an embodiment, the HOF includes trimesic acid.

In another aspect of the present disclosure, the HOF disclosed employs di- or tri-amine compounds and di- or tri-carboxylic acid compounds as organic linkers, wherein said linkers interact with one another and form hydrogen bonds, thus creating a framework comprising a multitude of interconnections forming a porous scaffold known as HOF. In some examples, the HOF includes aromatic di- or tri-amines and di- or tri-carboxylic acids as organic linkers. In some examples, the HOF includes aromatic di- or tri-amines and tri-carboxylic acids as organic linkers. In an embodiment, the HOF includes hydrogen bonded units of trimesic acid and guanazole.

In one embodiment, the HOF includes a tricarboxylic acid compound of formula I and a di-amine compound of formula II or a tri-amine compound of formula III to yield an HOF. The compounds of formulas I, II, and III are defined below:

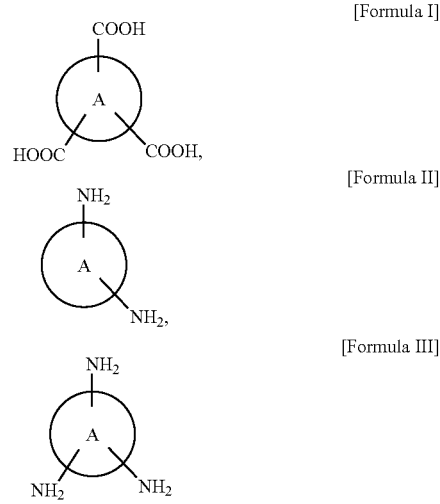

where: the ring A represents a 5- or 6-membered carbocyclic ring or a 5- or 6-membered heterocyclic ring. In a non-limiting example, the 5- or 6-membered heterocyclic ring may be selected from a group consisting of the formulas from a-h.

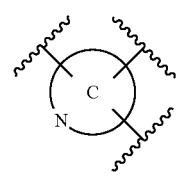

-continued

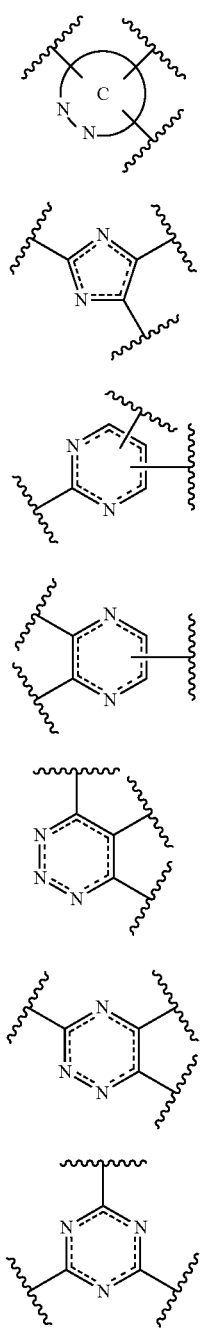

where: the wavy line (〜) indicates the point of attachment to the carboxy groups or amine groups of the formulas I, II, and III the dashed lines (·····) in any of the formulae from c-h represent single or double bonds; and, the ring C together with nitrogen (N) atom(s) form(s) a non-aromatic or an aromatic hydrocarbon ring in a and b. In a non-limiting example, the ring C of formula a may be selected from a pyrrolidine derivative, a pyrroline derivative, a pyrrole derivative, a piperidine derivative, or a pyridine derivative. In a non-limiting example, the ring C of formula b may be selected from a pyrazolidine derivative, a pyrazoline derivative, a pyrazole derivative, a pyridazine derivative. Further, it is contemplated that one or more N hetero atoms in formulae a-h may be replaced by any other suitable heteroatom, for example, but not limited to, oxygen (O), and sulfur (S).

The HOFS, according to the present disclosure, may comprise a single type of organic linker or two different types of organic linkers. It is contemplated that the hydrogen bond formation promoting functional group(s) attached directly or indirectly to the chemical structure of one type of organic linker, may interact with other organic linkers of same type and create intermolecular H-bonds. It is also contemplated that the hydrogen bond formation promoting functional group(s) attached directly or indirectly to the chemical structure of one type of organic linker, may interact with other organic linkers of different type and create intermolecular H-bonds. It is further contemplated that the hydrogen bond formation promoting functional group(s) attached directly or indirectly to the chemical structure of one type of organic linker, may interact with electronegative atoms (if any) present in the chemical structures of other organic linkers of same or different type and create intermolecular H-bonds.

In an embodiment, the HOF formed by hydrogen bonded units of trimesic acid and guanazole, is labeled as the KFUPM-HOF. In an embodiment, the KFUPM-HOF has a sheet structure, where the sheets form an intercrossed macroporous network with pores on a surface. The sheet structures may have a thickness ranging from 1-15 nm, preferably 2-13 nm, 4-10 nm, 6-8 nm, or approximately 7 nm. In an embodiment, the sheets are thicker than 15 nm. Further, the pores of the resulting HOF may have a diameter ranging from 100-1,000 nm, preferably 200-900 nm, 300-800 nm, 350-750 nm, 400-700 nm, 450-650 nm, 500-600 nm, or approximately 550 nm. Furthermore, the KFUPM-HOF may exhibit stability up to 280° C., preferably 230-280° C., 240-270° C., or 250-260° C.

In an embodiment, the HOF is substantially crystalline. In an embodiment, the HOF is at least 50% crystalline, preferably 60%, 70%, 80%, 90%, or 100%. In an embodiment, the KFUPM-HOF synthesized with trimesic acid and guanazole, exhibits a powder X-ray diffraction (PXRD) peak at 6.5-8°, preferably 6.8-7.8°, or 7-7.5°, a peak at 15-16.5°, preferably 15.5-16.2°, or 15.7-16°, a peak at 18.5-21°, preferably 19-20.5°, or 19.5-20°, a peak at 20-22.5°, preferably 20.5-22°, or 21-21.5°, a peak at 25-27°, preferably 25.5-26.5°, or 26-26.2°, a peak at 27-28°, preferably 27.2-27.8°, or 27.4-27.6°, a peak at 28-30°, preferably 28.5-29.5°, or 29-29.2°, a peak at 37-39°, preferably 37.5-38.5°, or 38-38.2° and 43-45°, preferably 43.5-44.5°, and 44-44.3°. In some embodiments, no PXRD peaks of trimesic acid and guanazole are present, indicating that all units are hydrogen bonded. In an aspect of the present disclosure, the HOF obtained is substantially pure and does not comprise any non-hydrogen-bonded guanazole or trimesic acid. In an embodiment, a portion of the guanazole is not hydrogen bonded to the trimesic acid. In an embodiment, 1-10%, preferably 2-8%, or 3-5% of the guanazole is not hydrogen bonded.

In some embodiments, the trimesic acid and guanazole may be mixed in any stoichiometric ratio. In a non-limiting example, trimesic acid and guanazole may be mixed in a molar ratio such that the guanazole is at least 10 times, at least 9 times, at least 8 times, at least 7 times, at least 6 times, at least 5 times, at least 4 times, at least 3 times, or at least 2 times the trimesic acid. In another non-limiting example, the trimesic acid and guanazole may be mixed in a molar ratio such that the trimesic acid is at least 10 times, at least 9 times, at least 8 times, at least 7 times, at least 6 times, at least 5 times, at least 4 times, at least 3 times, or at least 2 times the guanazole. In another non-limiting example, the trimesic acid and guanazole may be mixed in a 1:1 molar ratio.

The HOF may be prepared in one-pot by dissolving trimesic acid in water at 50-80° C., preferably 55-75° C., or 60-70° C. to form a trimesic acid solution. In some examples, the temperature is slowly increased at least till 60° C., 65° C., or 70° C. while stirring until complete dissolution of the trimesic acid is achieved. Also, separately dissolving guanazole in water to form a guanazole solution. In a non-limiting example, the concentration of the guanazole solution and the trimesic acid solution can be selected, independently, from a range from about 0.01 M to about 100 M, from about 0.5 M to about 75 M, from about 0.25 M to about 50 M, from about 0.1 M to about 25 M, from about 1 M to about 10 M, or from about 5 M to 10 M. Then adding dropwise the guanazole solution to the trimesic acid solution at a temperature of 50-80° C., preferably 55-75° C., or 60-70° C. to form a reaction mixture. In an embodiment, the trimesic acid solution, during the dropwise addition of the guanazole solution, is stirred, preferably in a continuous manner, at a rate of 600-800 RPM, preferably 650-750 RPM, or 700-725 RPM. In some examples, the addition of the guanazole solution into the trimesic acid solution to form the reaction mixture is performed rapidly i.e., the guanazole solution is poured in all in one step without dropwise addition. In an embodiment, the HOF synthesis does not require an organic solvent. Cooling the reaction mixture to 20-40° C., preferably 25-35° C. or approximately 30° C. to form a precipitate. The cooling requires the reaction mixture to be at least below 60° C. to form the precipitate. In some examples, the solution is cooled below 50° C. to form the precipitate. In some examples, the solution is cooled below 40° C. to form the precipitate. The cooling of the solution may be achieved through any known passive or active cooling methods. In some examples, the solution is cooled naturally by dissipation of heat from the solution in ambient conditions.

The precipitate may be separated and dried to yield the HOF. Separating and drying the precipitate involves the separation of the precipitate from the solution by any of the known methods, for example, but not limited to, gravity filtration, vacuum filtration, centrifugal filtration, mechanical filtration, or decanting. The drying of filtrate is carried out at an elevated temperature of, for example, but not limited to, at least 50° C., at least 55° C., at least 60° C., or at least 65° C. In an example, the drying is performed at temperature of at least 60° C. In some examples, the drying may be carried out in a vacuum oven. In an embodiment, the HOF is further ground into a powder and further dried at a temperature of 50-80° C., preferably 55-75° C., or 60-70° C., prior to contacting with water. In an embodiment, the grinding into a powder is with any method known in the art such as but not limited to, a mortar and pestle. In an embodiment, the HOF powder is packaged in any material known in the art that allows for permeation of water but does not dissolve on contact with water, such as a material made from polyethylene fibers. In an embodiment, the HOF powder is packaged in a semipermeable membrane which allows for diffusion of water into the packaging to be absorbed by the HOF but does not allow for penetration by other substances such as but not limited to dyes, humic substances, phenolic compounds, petroleum, surfactants, pesticides, and pharmaceuticals.

In a particularly preferred embodiment of the invention the HOF is dispersed in a sintered matrix. The sintered matrix is preferably an organic matrix such as carbon flake, graphite, or other forms of carbon. The HOF is uniformly dispersed in the sinterable matrix which is then subject to sintering at elevated temperature. The sintering forms a porous material in which the HOF is dispersed throughout and is exposed on open surfaces of the sintered carbon-based matrix. The sinterable matrix material is present in a mass ratio of from 1:1 to 10:1 with respect to the mass of the HOF and is preferably present in a major amount such as 1.1:1, 1.5:1, 2:1, 3:1, 4:1 or 5:1.

In an embodiment, the HOF on contact with the water, absorbs at least a portion of the water in the mixture. In an embodiment, the weight ratio of HOF to water in the mixture is 1 to 100-1,000, preferably 200-900, 300-800, 400-700, or 500-600. In another embodiment, the HOF has a maximum water uptake capacity of 650 mL per gram of HOF, preferably 500-650 mL/g, or approximately 600 mL/g. In other words if 1 g of HOF is added to 650 mL of water, 100% of the water will be absorbed by the HOF. In an embodiment, the water uptake or water sorption with the HOF of the present disclosure is 600 times its weight, preferably 600-800, or 650-700. In an embodiment, if the water comprises ions, the intercrossed macroporous network structure of the HOF is maintained in the presence of the ions in the water. In an embodiment, the mixture of the HOF and water is heated to a temperature of 50-100° C., preferably 60-90° C., or 70-80° C.

At step 104, method 100 includes separating the HOF from the mixture to leave a wet HOF. The wet HOF is the HOF with absorbed water from step 102. In an embodiment, the wet HOF may be separated by any method in the art, including filtering, and decanting. In an embodiment, the wet HOF has an expanded appearance, similar to that of cotton balls in water.

At step 106, method 100 includes drying the wet HOF at a temperature of at least 60° C., preferably 60-80° C., or approximately 70° C., for 12-24 hours, preferably 14-22 hours, 16-20 hours, or approximately 18 hours to form a recycled HOF. In an embodiment, the drying is facilitated by an oven. In an embodiment, the drying removes water that was absorbed in step 102. In an embodiment, the water removed in the drying step can be recaptured separately from the HOF. In an embodiment, the water is removed from the HOF in order to repeat the steps 102 and 104, referred to as recycling. In an embodiment, the weight of the recycled HOF is 10%, preferably 5%, 1%, or 0%, less than the weight of the HOF added in step 102. In an embodiment, a portion of the HOF may be lost in the recycling process.

At step 108, method 100 includes recycling the HOF up to 10 times, preferably 5-10, or 8-9 times following the steps of water absorption and drying. In other words, steps 102-106 are repeated up to 10 times. In an embodiment, the intercrossed macroporous network structure of the HOF is maintained following recycling. In an embodiment, the water absorption capacity of the HOF is maintained following recycling. In other words, no decrease in water absorption capacity was observed on using the recycled HOF for water absorption.

The HOF of the present disclosure has strong ability to adsorb water, and therefore it can be employed as a hygroscopic material in a multitude of applications, including but not limited to chemical heat pumps, humidity control systems, and as a desiccant. In an embodiment, the HOF of the present disclosure, can be used in a humidity control system. The humidity control system includes a hygroscopic material, and an air supply, which may include water vapor. A humidity control system can be used for the dehumidification or moisture control of vehicles, residences, and production facilities. In an embodiment, air containing a relatively large amount of water vapor, preferably greater than 50% humidity, is supplied from the outside and passes over the HOF, where least a portion of the water vapor in the air in then is adsorbed and removed. In an embodiment, the humidity control system is attached to an air conditioning unit.

In an embodiment, the HOF can be used as a reusable desiccant. In an embodiment, the HOF powder packaged, as previously described can be used as a desiccant in similar applications to that of silica gel. In an embodiment, the HOF is used as a desiccant with electronics, medicine, and packaging to prevent mold or water damage. In an embodiment, after the HOF has reached its maximum capacity for water absorption it can then be recycled and reused through the steps described in the method 100 of the present disclosure.

In another embodiment, the HOF can be used in an atmospheric water generator. In an embodiment, the HOF of the present disclosure absorbs the ambient humidity. Then the atmospheric water generator system extracts the water from the HOF in a method similar to that of step 106 described in the present disclosure. This water can then be purified for consumption, through processes such as passing the water through a membrane and/or filtering the water. In an embodiment, the atmospheric water generator is run with electricity from a renewable energy source, such as wind, or solar power. By absorbing water from the air and generating potable drinking water, water can potentially be harvested in regions of the world where clean water is needed. Specifically, due to the ease of synthesis and high water uptake capacity of the HOF of the present disclosure, this method could be implemented in any region of the world.

EXAMPLES

The following examples describe and demonstrate exemplary embodiments of the method 100 of increasing water uptake with the HOFs of the present disclosure, as described herein. The examples are provided solely for illustration and are not to be construed as limitations of the present disclosure, as many variations thereof are possible without departing from the spirit and scope of the present disclosure.

Chemicals

The commercially available reagents were employed and used as received without further purification. Trimesic acid (TMA, 95%) and 3,5-diamino-1,2,4-triazole (GZ, 98%) were purchased from Sigma-Aldrich. Tap water was taken from the laboratory tap, and deionized (DI) water with a resistivity of 18.3 was used to prepare all the solutions.

Methods $^1$ and $^{13}C$ NMR spectra were recorded on a Bruker AM-400 spectrometer using TMS (tetramethylsilane) as the internal standard. Powder X-ray diffraction (PXRD) patterns of the samples were recorded using a Rigaku MiniFlex diffractometer equipped with Cu Kα radiation. The data were acquired over the 2θ range of 5 and 60°. The Fourier-transform infrared spectra (FT-IR) were obtained using a Nicolet 6700 Thermo Scientific instrument in 400-4000 $cm^{-1}$. Field Emission Scanning Electron Microscope (FE-SEM, Tescan Lyra-3 Dual Beam instrument) equipped with an Energy Dispersion Spectrometer (EDX, Oxford Instruments) was used to discern the morphological features and confirm the constituent elements. All the thermogravimetric mass loss profile curves were collected using a Metler-Toledo TGA. The samples were loaded into an alumina crucible, and the mass loss profile was collected under a constant Ar-flow of 20 mL min$^{-1}$ at a continuous ramp rate of 10° C. min$^{-1}$.

Example 1: Synthesis of HOFs

Figure 2:
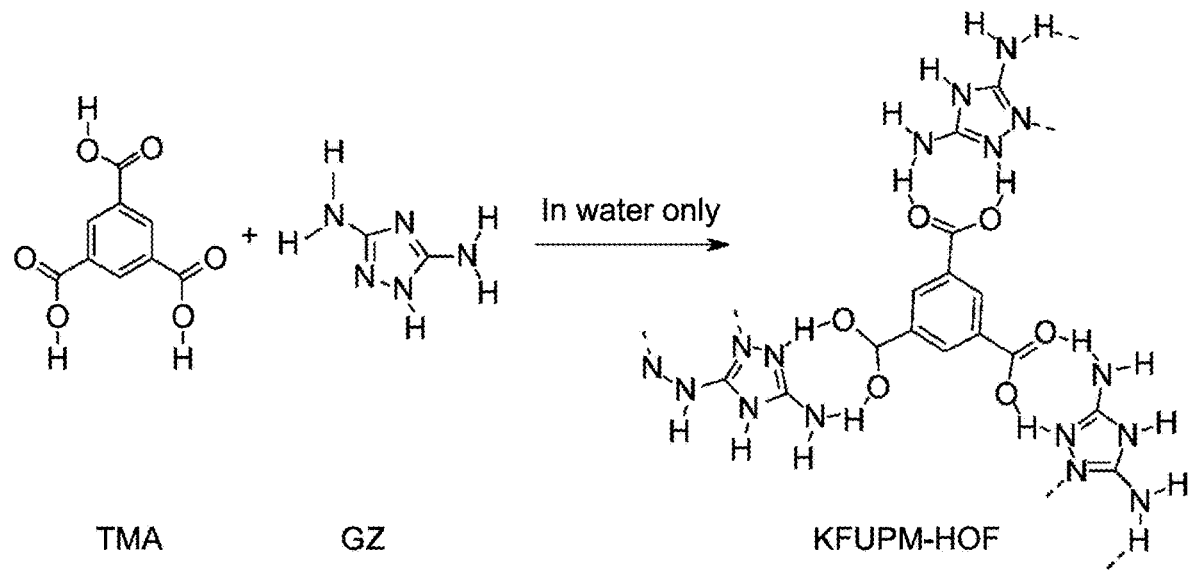
FIG. 2 is a schematic representation of a synthesis of HOF-KFUPM from precursors, trimesic acid (TMA) and 3,5-diamino-1,2,4-triazole (GZ), according to embodiments of the present disclosure.

A protocol for the synthesis of the KFUPM-HOF or HOF using water as a solvent is shown in FIG. 2. To obtain the HOF, the molar ratio of TMA and GZ was set to 1:1. For a typical synthesis of KFUPM-HOF, an aqueous TMA (6.0 mmol) solution was prepared by dissolving TMA in Milli-Q water, in a round bottom flask, with constant stirring, at room temperature. The temperature was increased slowly to 70° C. with continuous stirring until the complete dissolution of the TMA. Similarly, an aqueous solution of the GZ was prepared separately by dissolving GZ (6.0 mmol) in Milli-Q water. Further, both solutions, i.e., the TMA and GZ solutions, were mixed by dropping the GZ solution into the TMA solution while continuous stirring. The resultant solution was removed from the hot plate and allowed to cool naturally. When the temperature of the solution reached around 40° C., the formation and precipitation of a white solid were observed. A vacuum oven filtered the white precipitate and dried at 65° C. in a vacuum oven. The yield of the KFUPM-HOF was found to be more than 95%.

Example 2: Morphology and Microstructure Analysis

Figure 3A:
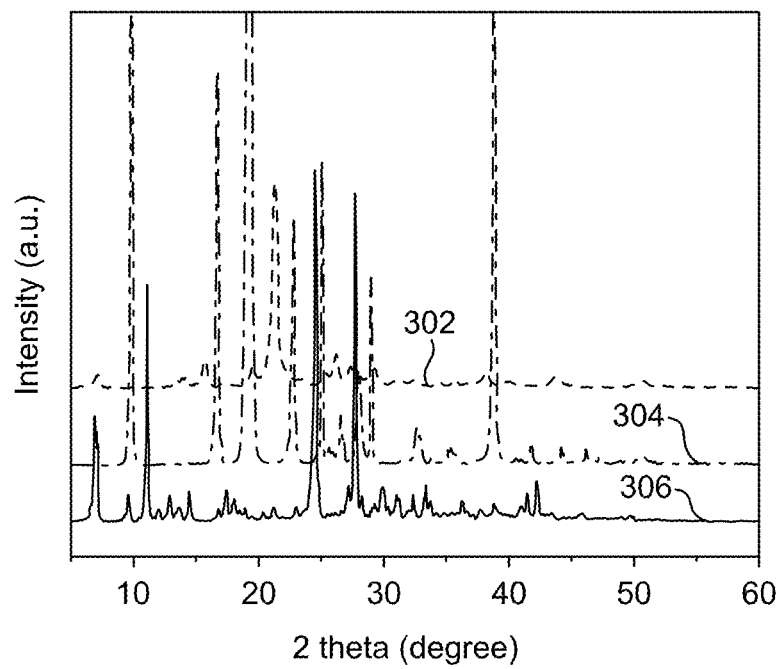
FIG. 3A shows powder X-Ray Diffractogram (PXRD) plots of TMA, GZ, and KFUPM-HOF, according to embodiments of the present disclosure.

The Powder X-ray diffraction (PXRD) measurements were conducted to determine the crystalline structures of as-synthesized HOF samples. The diffractogram depicts crystalline HOF structures with barely any amorphous background, as evidenced by their sharp reflections in FIG. 3A. FIG. 3A shows the XRD diffractogram of TMA (302), GZ (304), and KFUPM-HOF (306), respectively. From the FIG. 3A, it can be observed that for KFUPM-HOF (306), the major peaks were observed at 7.2°, 15.7°, 19.5°, 21.3°, 26.2°, 27.4°, 29.2°, 38.2° and 43.8° of which the peak at 21.3° was the most intense. Some minor and rather broad reflections were observed between 10° and 35° . No peaks characteristic of the TMA (302) or GZ (304) were observed in the spectra of KFUPM-HOF samples.

Figure 3B:
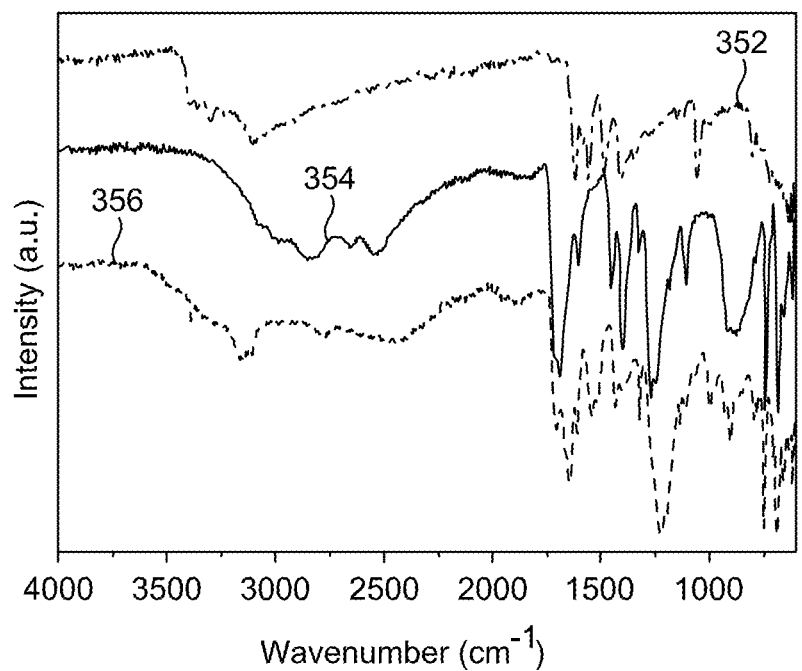
FIG. 3B depicts Fourier Transform Infrared (FT-IR) spectra of TMA, GZ, and KFUPM-HOF, according to embodiments of the present disclosure.

The FT-IR spectra for the samples GZ (352), TMA (354), and the KFUPM-HOF (356) were performed; the results of this study are depicted in FIG. 3B. From the FIG. 3B, several distinct peaks of both acid (TMA) and amine (GZ) in KFUPM-HOF were observed. The peak at 3383 $cm^{-1}$ corresponding to the N—H stretching vibration for the amine was found at 3389 $cm^{-1}$ in the case of the KFUPM-HOF. The peak at 3096 $cm^{-1}$ corresponds to the N-H stretching vibration for the amino group shifted to 3153 $cm^{-1}$ in the case of KFUPM-HOF due to hydrogen bonding with the trimesic acid. The strong —OH stretching vibration peak of the acid at 2813 $cm^{-1}$ and 2535 $cm^{-1}$ were shifted to 2430 $cm^{-1}$ due to hydrogen bonding between the GZ and the TMA. In TMA, the peak at 1692 $cm^{-1}$ corresponds to the peak of the carbonyl group of the acid. In KFUPM-HOF, this peak was observed at 1640 $cm^{-1}$ due to its involvement in the hydrogen bonding with the amine. The peak at 1619 $cm^{-1}$ in the amine corresponds to the out-of-plane bending of $NH_2$, and the stretching vibration of the CN bond can also be observed at 1608 $cm^{-1}$ in the case of KFUPM-HOF. The peak at 1556 $cm^{-1}$ in the GZ is due to the out-of-plane bending of the CNH and $NH_2$ bond, which was also observed in KFUPM-HOF at 1546 $cm^{-1}$, confirming the presence of the amine in it. Furthermore, the stretching vibration of the ring CN bond in the GZ at 1477 cm$^{-1}$ is also observed in KFUPM-HOF at 1430 cm$^{-1}$ due to hydrogen bonding.

Figure 3C:
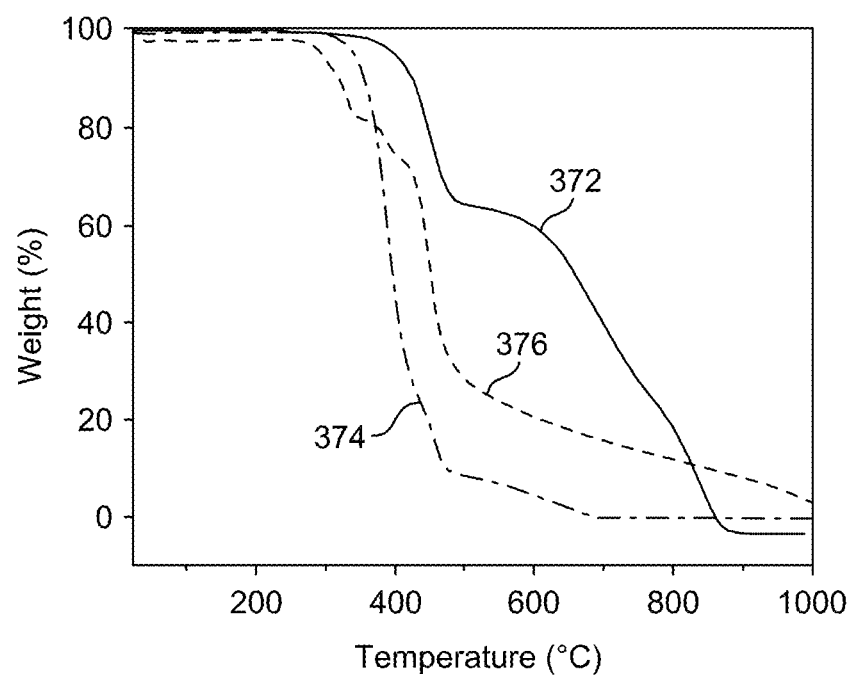
FIG. 3C depicts thermogravimetric analysis (TGA) plots for TGA of TMA, GZ, KFUPM-HOF, according to embodiments of the present disclosure.

Thermogravimetric analysis (TGA) was used to compare the mass-loss profiles of the precursors (TMA and GZ) and the resultant KFUPM-HOF structure under N$_2$ flow, and the curves are presented in FIG. 3C. Two weight-loss stages were observed for KFUPM-HOF (376). The initial weight loss of about 1-3% at 100-120° C. was likely due to the moisture present in the HOF network, while the second weight loss which started around 280° C. (higher than the GZ (374) and lower than TMA (372) was due to the thermal degradation of the KFUPM-HOF structure. The different thermal behavior observed by the KFUPM-HOF compared to its precursors (GZ and TMA) confirms the formation of a new intermediate structure, by intermolecular hydrogen bonding.

Figure 4:
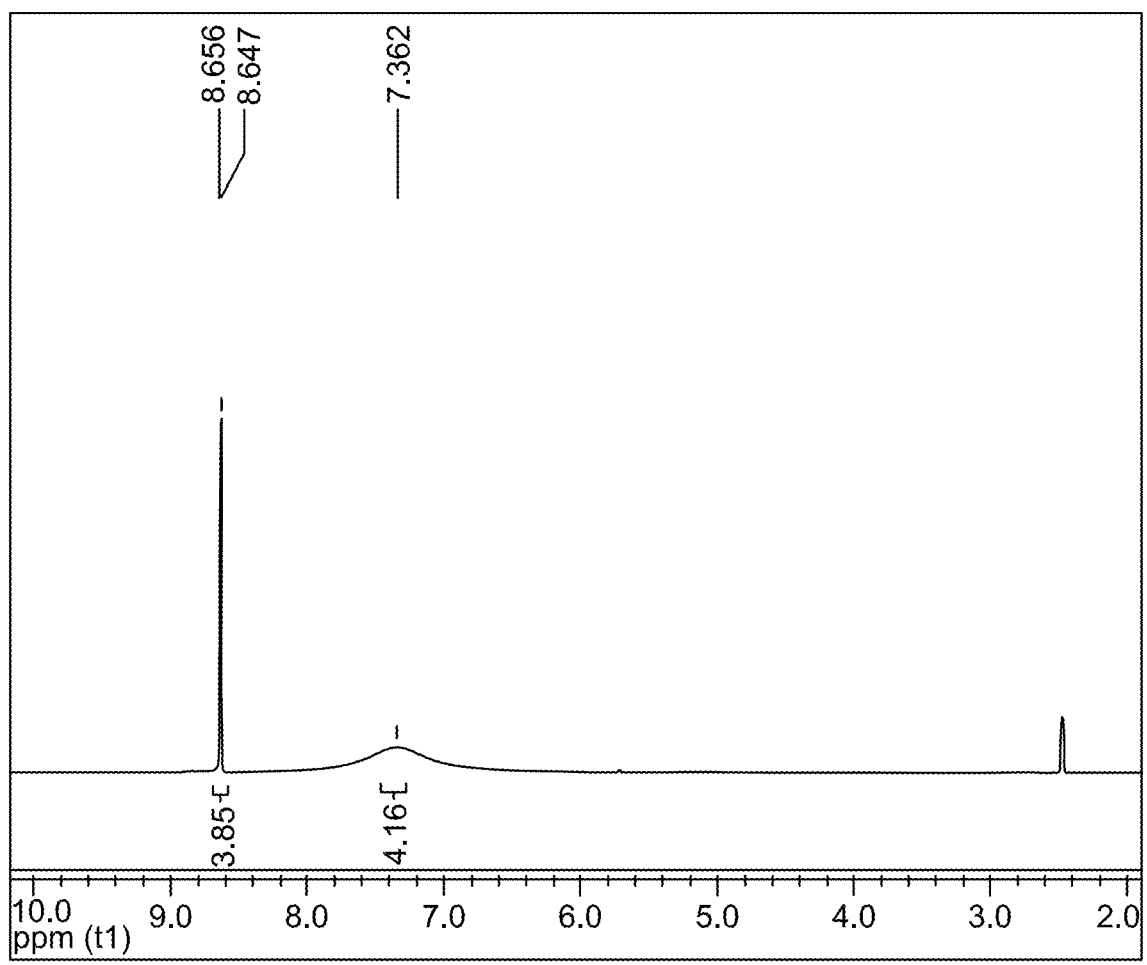
FIG. 4 shows a $^1$H-nuclear magnetic resonance (NMR) of KFUPM-HOF, according to embodiments of the present disclosure.
Figure 5:
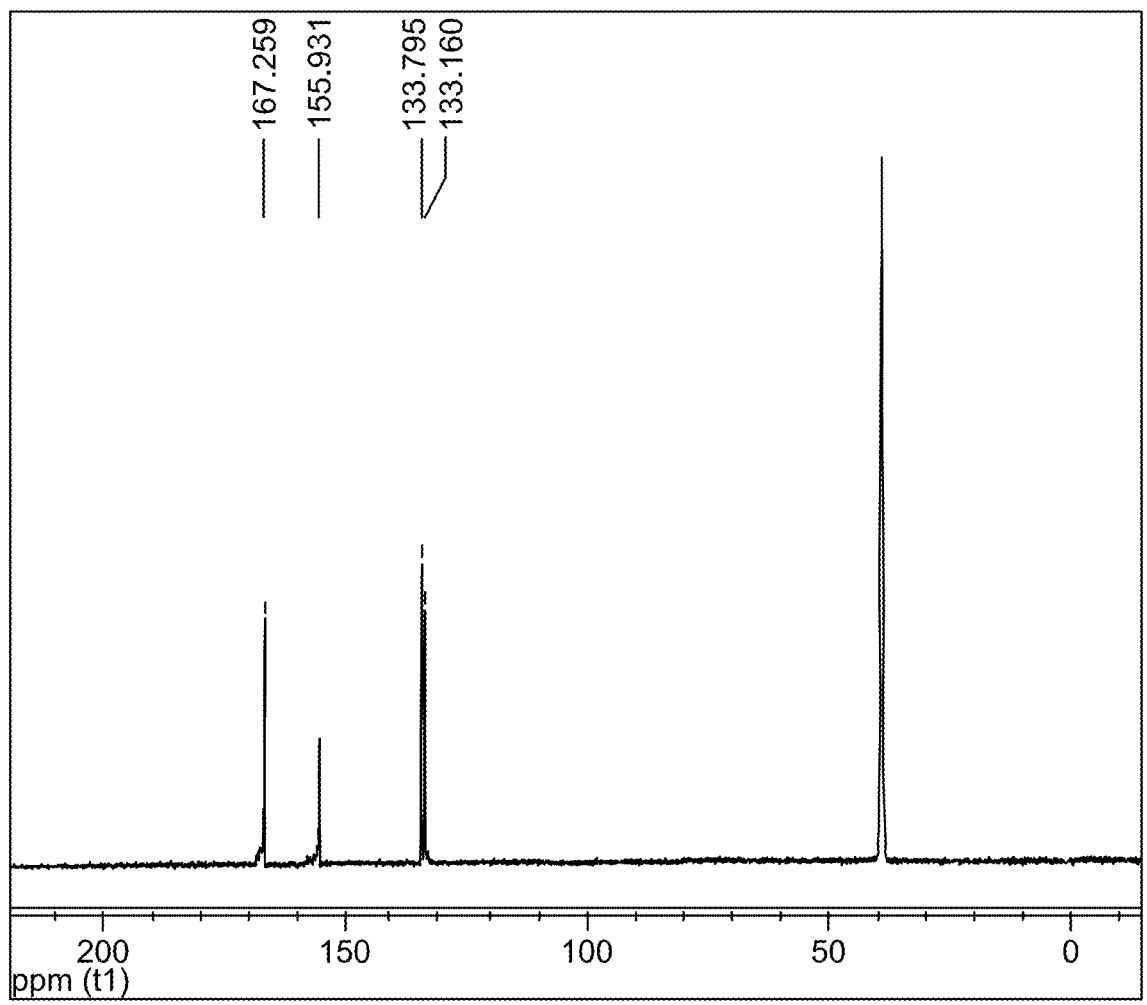
FIG. 5 shows a $^{13}$C-NMR of KFUPM-HOF, according to embodiments of the present disclosure.

The $^1$H NMR and $^{13}$C NMR spectra of KFUPM-HOF are depicted in FIG. 4 and FIG. 5. $^1$H NMR (DMSO-d$_6$) δ 7.36 (s, 4H, —NH$_2$), 8.65 (s, 3H, Ar—H), 8.66 (s, 1H, NH). $^{13}$C NMR (DMSO- d$_6$): δ 133.2, 133.8, 155.9, and 167.2.

The FT-IR peaks of KFUPM-HOF are 3389, 3153, 2430, 1640, 1608, 1546, 1430, 1398, 1330, 1221, 990, 901, 786, 749, 687 cm$^{-1}$.

Figure 6A:
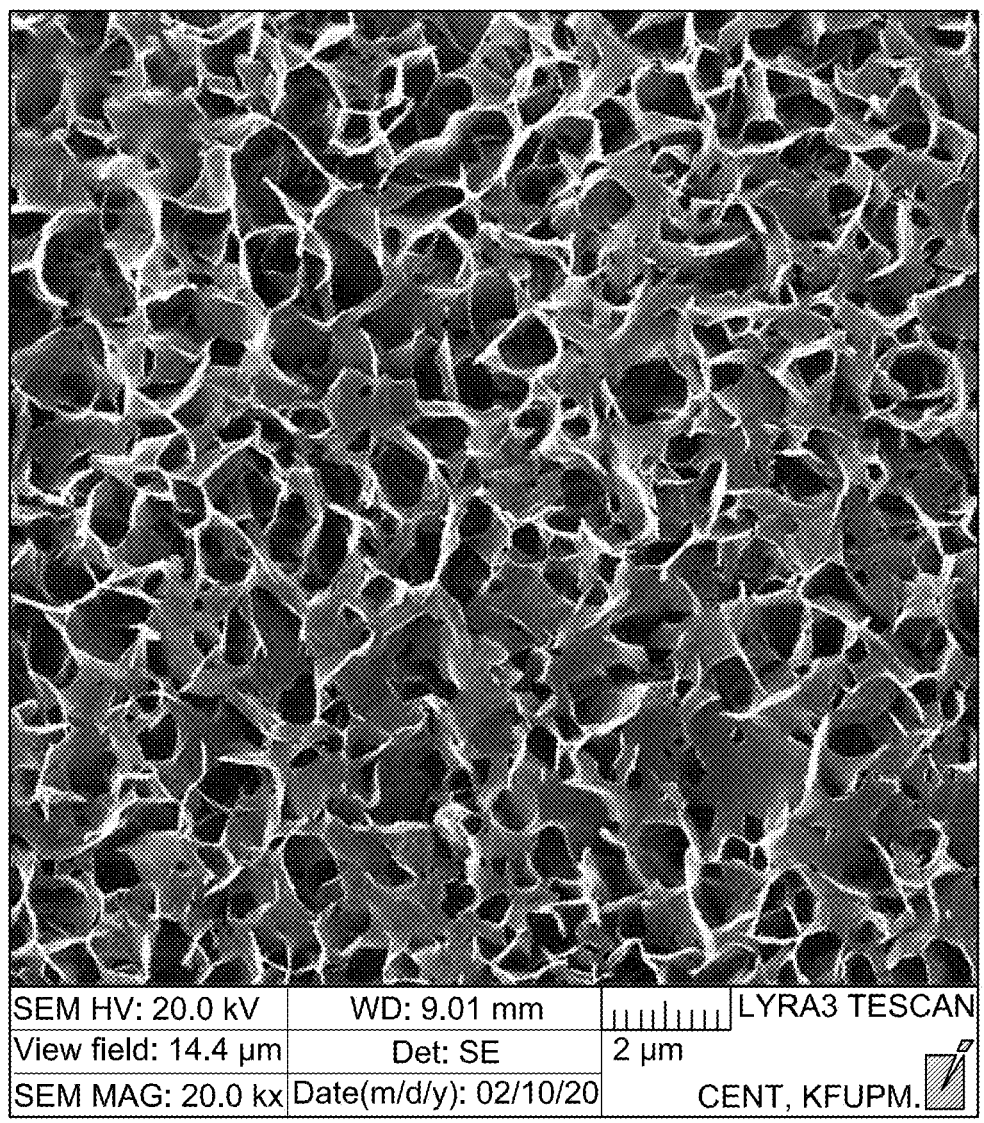
FIGS. 6A and 6B show scanning electron microscopic (SEM) images depicting low and high magnification of KFUPM-HOF, according to embodiments of the present disclosure.
Figure 6B:
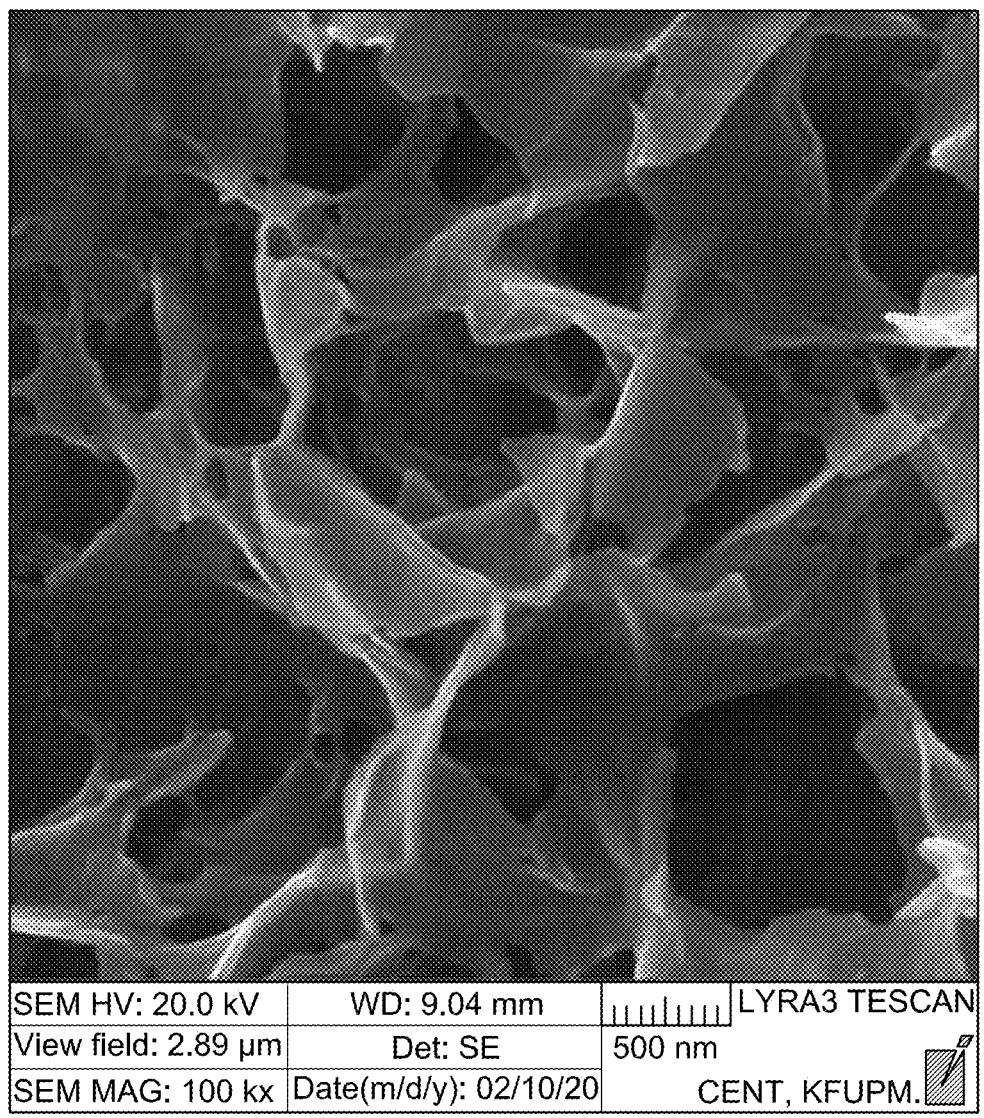
Figure 7:
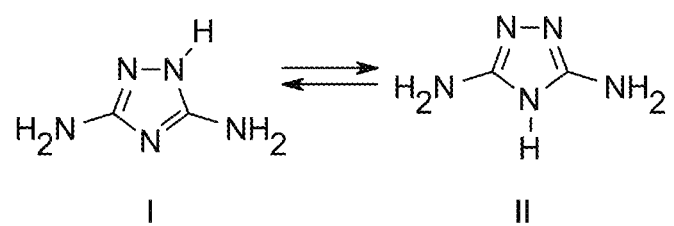
FIG. 7 depicts the tautomeric forms of GZ, according to embodiments of the present disclosure.

The morphological features of the synthesized HOF structures were investigated by Field Emission Scanning Electron Microscopy (FE-SEM). FIG. 6A shows a typical low-magnification micrograph of the KFUPM-HOF, revealing that the sample consists of a hierarchical microporous network of sheet-like structures with wide pores on the surface. A magnified image, as shown in FIG. 6B, recorded to reveal the porous network's detailed structure, clearly shows 2D sheets of thickness ~5-7 nm inter-crossed with each other. The amine GZ usually exists in two tautomeric forms, GZ I and GZ II (FIG. 7). In the case of free amine, the peaks of the —NH$_2$ are at 4.81 and 5.51 ppm due to its asymmetric nature, and the —NH peak at 10.74 ppm.

Figure 8:
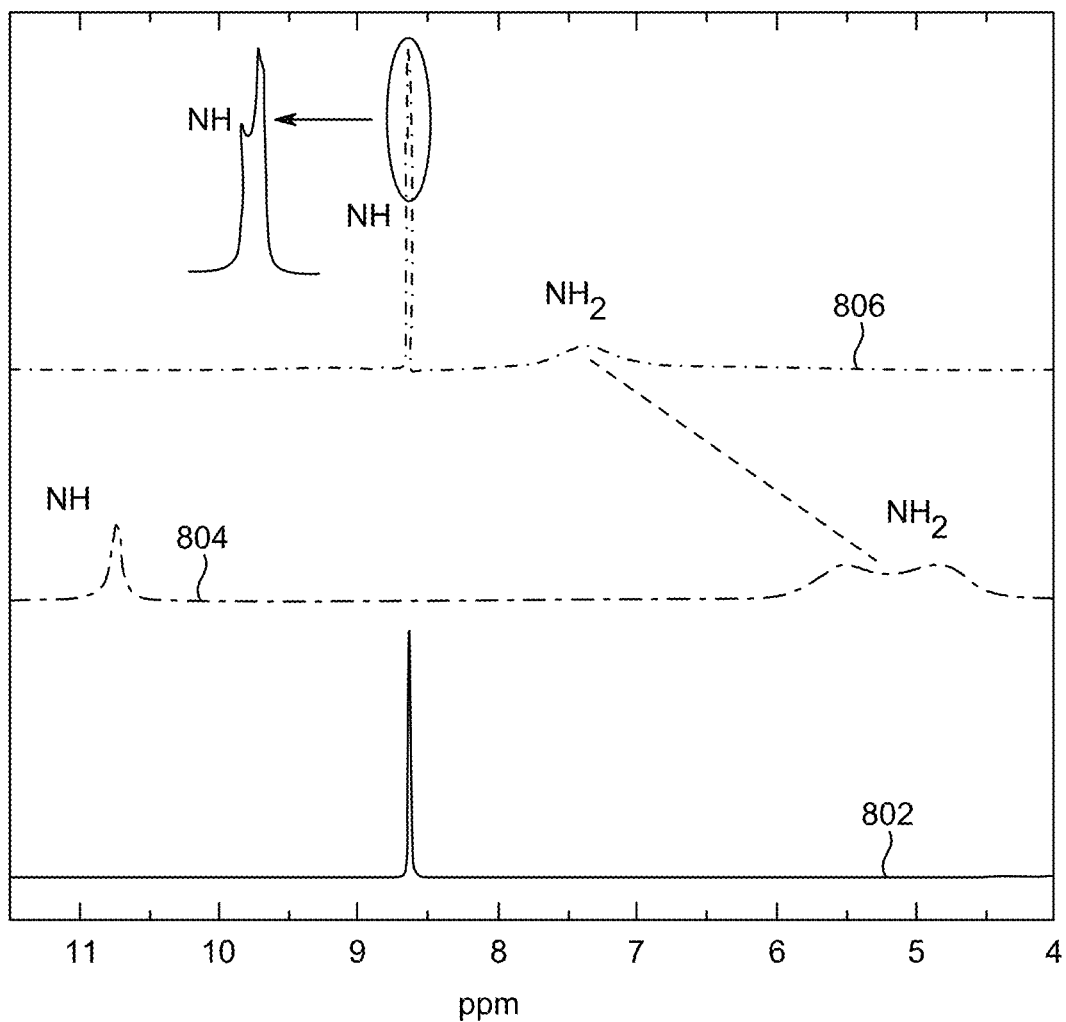
FIG. 8 shows a comparative partial $^1$HNMR of the TMA, KFUPM-HOF, and GZ, according to embodiments of the present disclosure.

In the formation of the KFUPM-HOF (806) with the TMA (802) and GZ (804) through hydrogen bonding between the hydrogen of the —NH$_2$ and the oxygen of the carboxylic acid, the peaks of the two NH$_2$ are shifted downfield to 7.36 ppm from 4.81 ppm and 5.51 ppm due to de-shielding as displayed in FIG. 8. Moreover, it is evident from the $^1$H (FIG. 4) and $^{13}$C NMR (FIG. 5) of KFUPM-HOF that tautomer II is more stable, resulting in asymmetric amine and one broad peak at 7.36 ppm for the two NH$_2$ groups. In the case of the NH proton of the amine ring (8.66 ppm), it is merged with the TMA peak (8.65 ppm) due to the tautomeric form GZ II (FIG. 7).

Example 3: Water Holding Capacity of the KFUPM-HOF

Figure 9A:
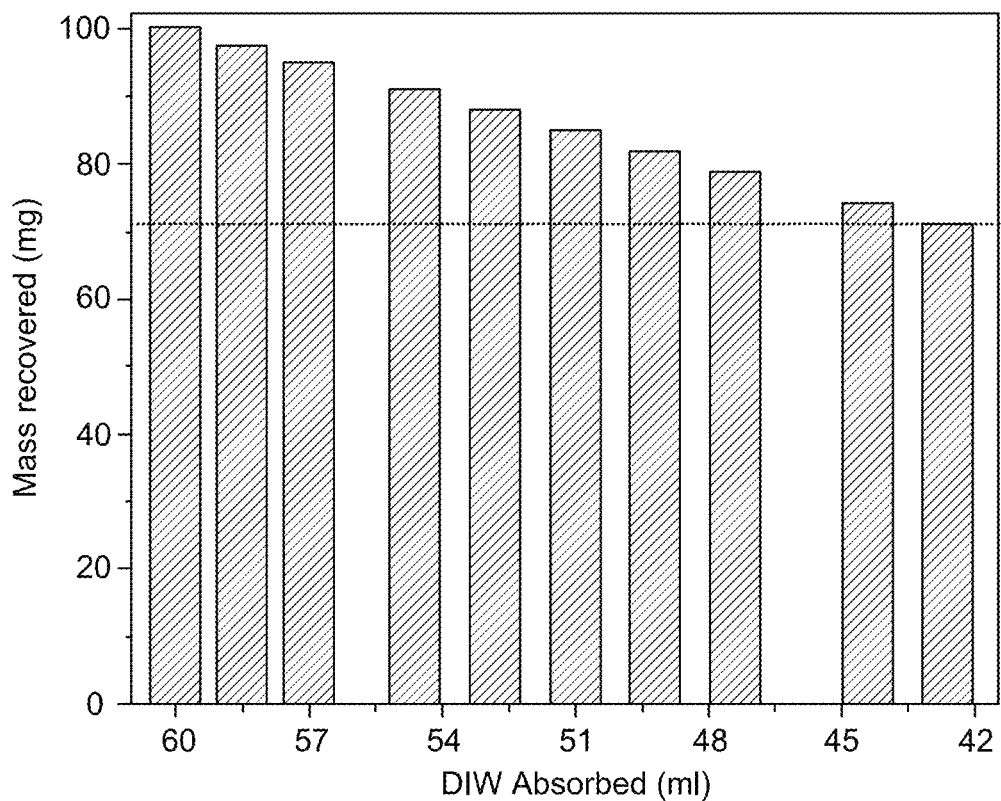
FIG. 9A depicts a DI water uptake of KFUPM-HOF, according to embodiments of the present disclosure.
Figure 9B:
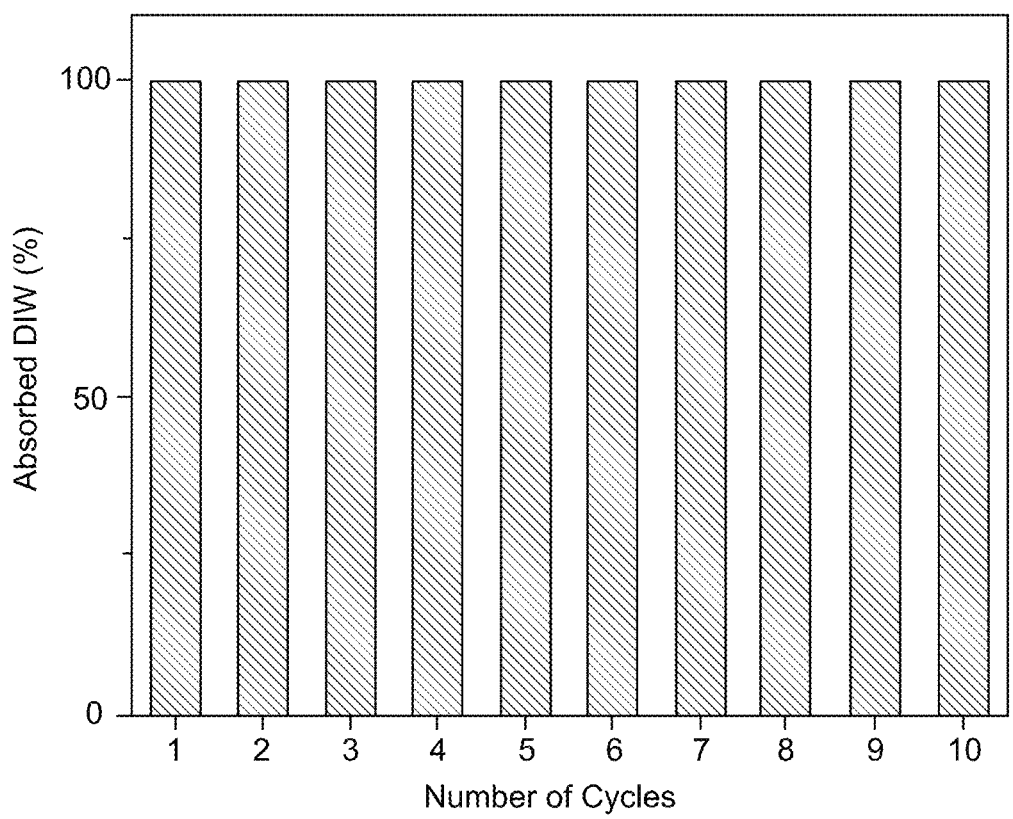
FIG. 9B depicts a percentage of water holding capacity up to 10 cycles, according to embodiments of the present disclosure.

The KFUPM-HOF, as prepared in Example 1, was further ground and dried under a vacuum oven at 65° C. for 24 h before testing its water holding capacity to ensure the exact amount of material. Experiments were conducted to evaluate the water holding capacity of the KFUPM-HOF without any activation. The calculated amount (100 mg) of KFUPM-HOF powder was weighed and added to 60 ml of water (de-ionized water or tap water) and heated slowly up to 70° C. with stirring until the complete dissolution of the powder. On complete dissolution, the flask was removed from the hot plate, kept unstirred, and allowed to cool naturally. It was observed that the nucleation of KFUPM-HOF started when the temperature of the solution reached around 40° C. The growth rate of KFUPM-HOF residue was found to increase as the temperature decreased naturally. The flask containing 60 ml of water appeared as soaked cotton balls in the water. The flask was further inverted to confirm if the water was retained in the KFUPM-HOF. The amount of water held by 100 mg of KFUPM-HOF is shown in Table 1 and FIG. 9A, which is around 600 times the weight of KFUPM-HOF. Moreover, the % water holding capacity was tested for up to 10 cycles; the results were found to be the same (FIG. 9B). However, a slight loss of KFUPM-HOF was observed after each cycle due to its solubility in water and material loss during the cycling process between the hydrated and dry states, as shown in Table 1.

TABLE 1

The amount of DI water uptake and water holding capacity of KFUPM-HOF

| Number of cycles | Mass of KFUPM-HOF (mg) | DI water uptake (ml) | Water holding capacity (%) |
| --- | --- | --- | --- |
| 1 | 100 | 60 | 600 |
| 2 | 97 | 58.5 | 600 |
| 3 | 95 | 57 | 600 |
| 4 | 91 | 54.6 | 600 |
| 5 | 88 | 52.8 | 600 |
| 6 | 85 | 51 | 600 |
| 7 | 82 | 49.2 | 600 |
| 8 | 79 | 47.4 | 600 |
| 9 | 74 | 44.4 | 600 |
| 10 | 71 | 42.6 | 600 |

Figure 10A:
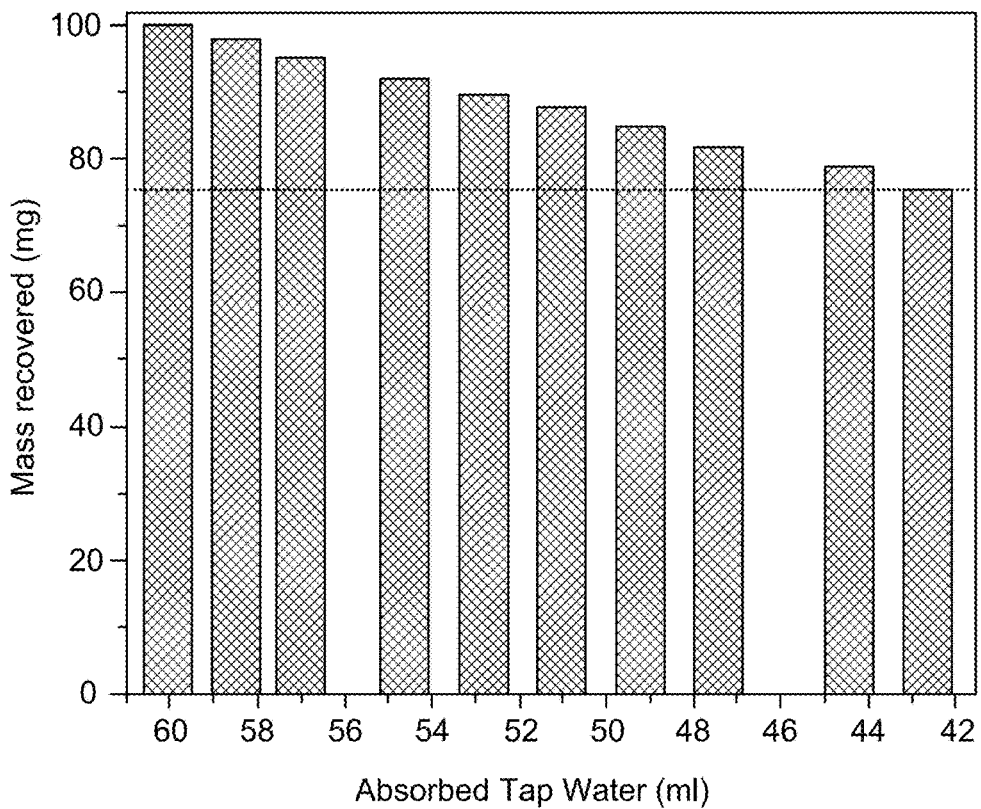
FIG. 10A depicts tap water uptake of KFUPM-HOF, according to embodiments of the present disclosure.
Figure 10B:
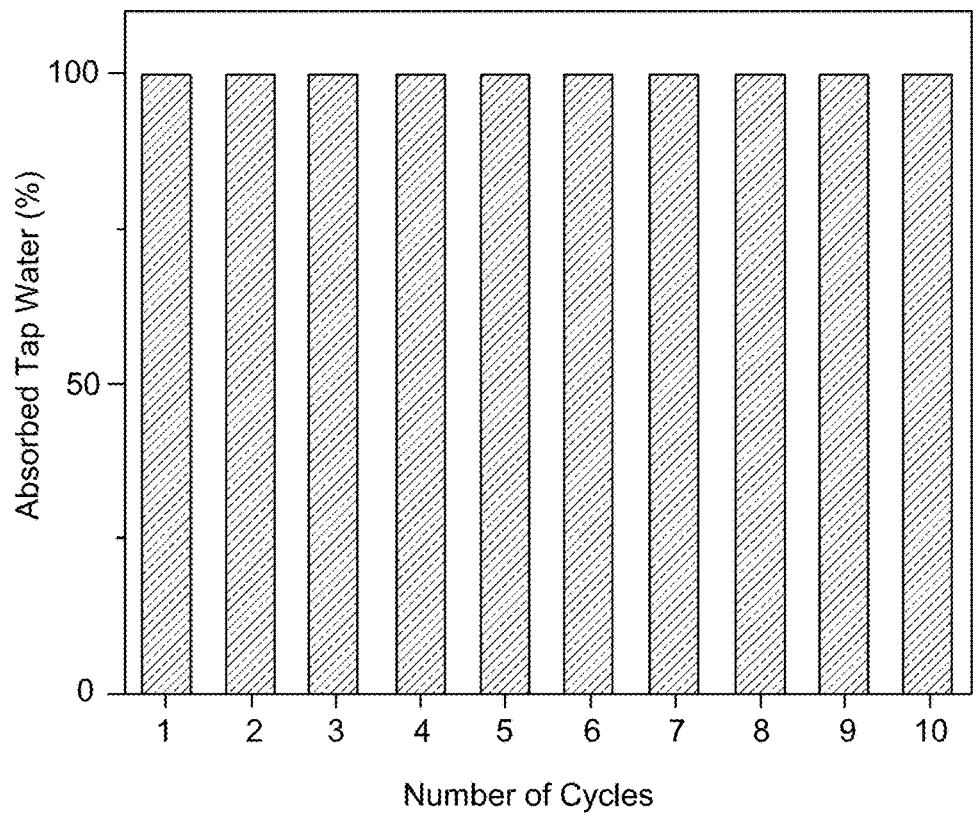
FIG. 10B depicts a percentage of water holding capacity up to 10 cycles, according to embodiments of the present disclosure.

The experiments were also conducted with tap water under the same conditions as used for DI water to test the behavior of KFUPM-HOF. The results of this study are presented in FIG. 10A. The tap water uptake by KFUPM-HOF was the same as observed in DI water, as shown in FIG. 10A. Moreover, the water holding capacity was retained for up to 10 cycles. However, loss of KFUPM-HOF was also observed but more minor than DI water (FIG. 10B).

Figure 11A:
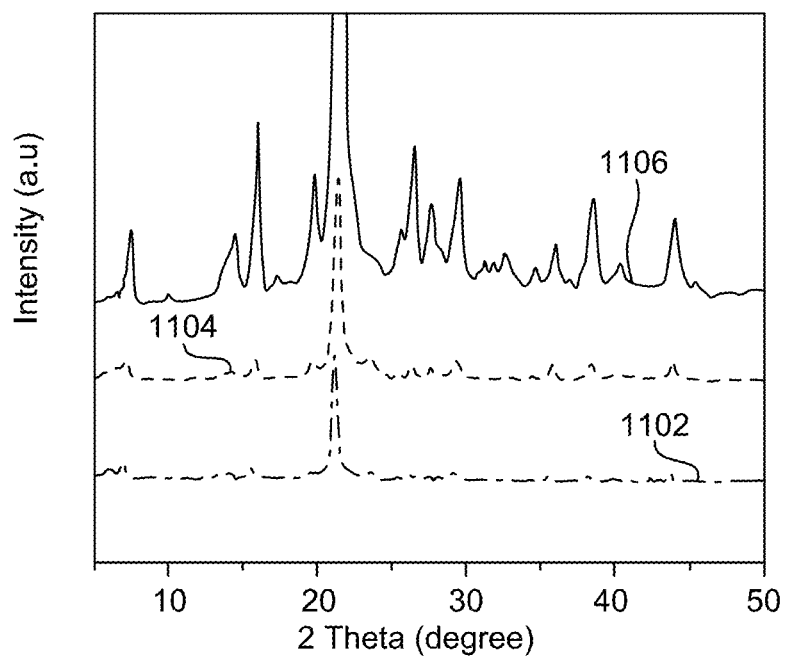
FIG. 11A shows a PXRD spectrum of KFUPM-HOF, recycled DI water KFUPM-HOF, and recycled tap water KFUPM-HOF, according to embodiments of the present disclosure.

The PXRD measurements of recycled samples, i.e., in DI water (1102) and tap water (1104), were compared with the pure sample, KFUPM-HOF (1106), as shown in FIG. 11A. The peaks in both the recycled samples were found at the same positions. However, the intensities of the peaks at the particular positions were found to be lower in the recycled samples compared to the pure sample. No other peak emerged or was detected during the recycling, confirming that the KFUPM-HOF retained its original structure with low crystallinity.

Figure 11B:
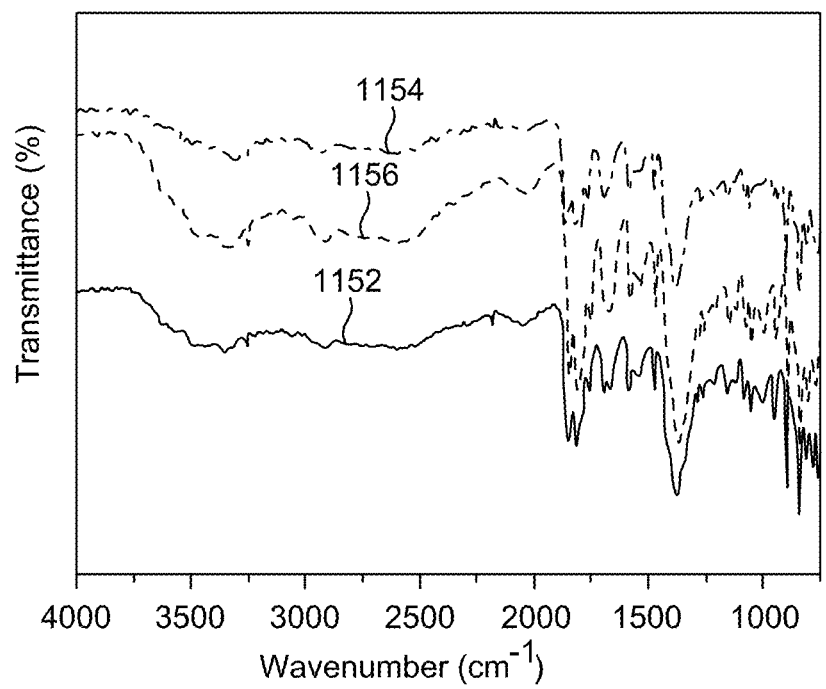
FIG. 11B depicts FT-IR spectra of KFUPM-HOF, recycled DI water KFUPM-HOF, and recycled tap water KFUPM-HOF, according to embodiments of the present disclosure.

Further, the FT-IR of the recycled samples, i.e., in DI water (1154) and tap water (1156), were conducted and compared to the pure KFUPM-HOF (1152), as shown in FIG. 11B. Identical peak positions of —NH and —OH stretching were observed in all the samples, i.e., the recycled and pure samples. The results confirm that the structural identity of the KFUPM-HOF was retained even after recycling in DI and tap water.

Figure 12A:
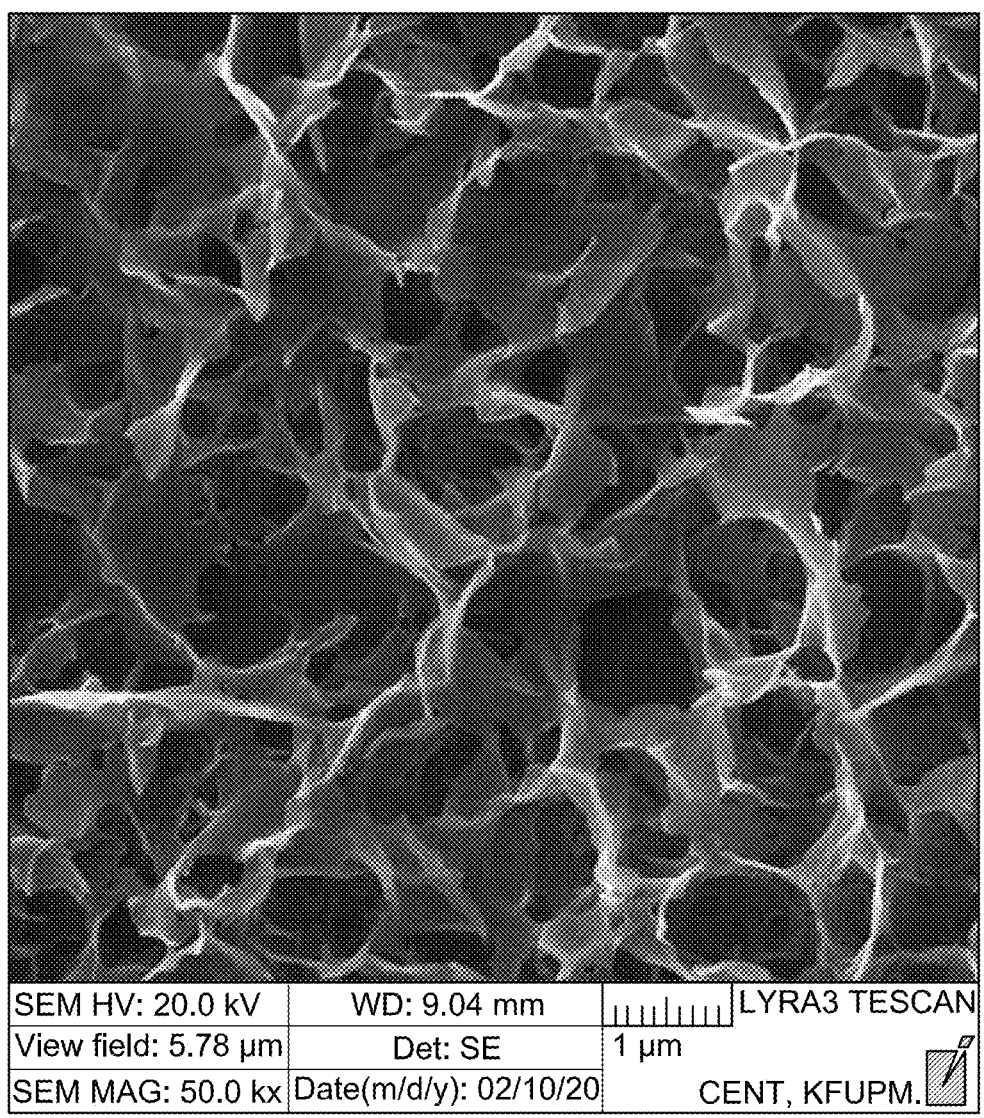
FIG. 12A-C shows a FE-SEM of KFUPM-HOF, recycled DI water KFUPM-HOF, and recycled tap water KFUPM-HOF, respectively according to embodiments of the present disclosure.
Figure 12B:
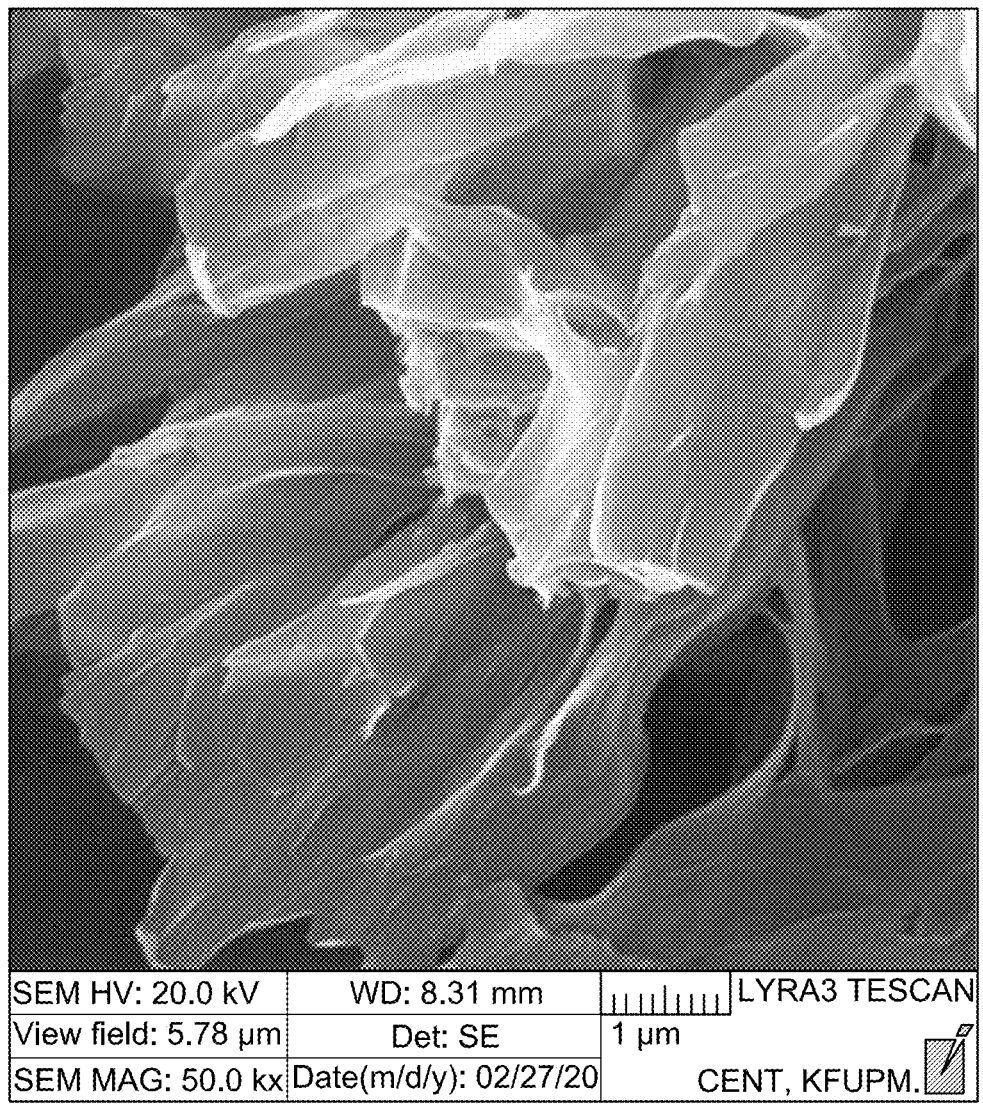
Figure 12C:
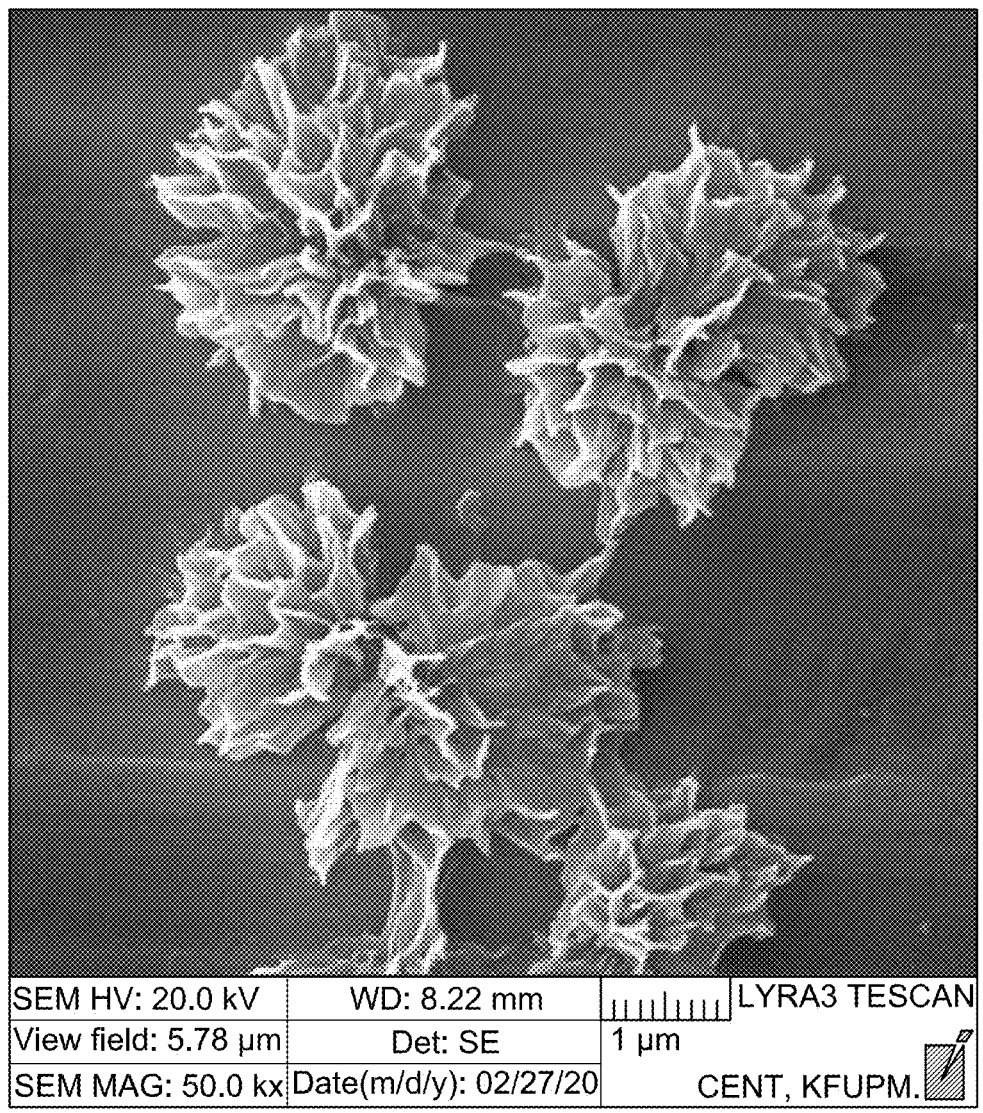

FE-SEM of pure KFUPM-HOF, recycled KFUPM-HOFS from DI and tap water were conducted to investigate the change in the morphological features of the pure synthesized HOF structures with the recycled KFUPM-HOFS. FIGS. 12A-12C depicts high magnification micrographs of the pure KFUPM-HOF (FIG. 12A), recycled KFUPM-HOFS from DI water (FIG. 12B), and tap water (FIG. 12C), respectively. The micrographs reveal that sheet type morphology of KFUPM-HOFS samples is retained.

KFUPM-HOF was synthesized in one step by a green approach. The mechanism of hydrogen bond formation between amine and acids moieties was elucidated. Relevant analytical techniques were used to characterize the extended framework. The HOF of the present disclosure is an excellent candidate for water uptake applications and can hold water 600 times its weight. Moreover, the structural features and water holding capacity did not change after ten cycles.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A method of water uptake, comprising:
   contacting a hydrogen-bonded organic framework (HOF) with water to form a mixture;
   wherein the HOF absorbs at least a portion of the water in the mixture;
   wherein the HOF comprises:
      hydrogen bonded units of trimesic acid and guanazole; and
      the HOF has a sheet structure;
         wherein the sheets form an intercrossed macroporous network with pores on a surface.

2. The method of claim 1, wherein the molar ratio of trimesic acid to guanazole in the HOF is 1-5 to 1-5.

3. The method of claim 1, wherein the molar ratio of trimesic acid to guanazole in the HOF is 1 to 1.

4. The method of claim 1, wherein the HOF is substantially crystalline.

5. The method of claim 1, wherein the sheets of the HOF have a thickness of 1-15 nm.

6. The method of claim 1, wherein the pores of the HOF have a diameter of 100-1,000 nm.

7. The method of claim 1, wherein the HOF is stable up to 280° C.

8. The method of claim 1, further comprising grinding the HOF into a powder and drying at a temperature of 50-80° C. prior to contacting with water.

9. The method of claim 1, further comprising heating the mixture to a temperature of 50-100° C.

10. The method of claim 1, wherein the weight ratio of HOF to water in the mixture is 1 to 100-1,000.

11. The method claim 1, wherein the HOF has a maximum water uptake capacity of 650 mL per gram of HOF.

12. The method of claim 1, wherein the water comprises at least one ion selected from the group consisting of calcium, bicarbonate, magnesium, sodium, potassium, chloride, nitrate, and sulfate.

13. The method of claim 12, wherein the intercrossed macroporous network structure of the HOF is maintained in the presence of at least one ion in the water.

14. The method claim 1, further comprising:
   separating the HOF from the mixture to leave a wet HOF; and
   drying the wet HOF at a temperature of at least 60° C. for 12-24 hours to form a recycled HOF.

15. The method claim 14, further comprising recycling the HOF up to 10 times following the steps of water absorption and drying.

16. The method claim 15, wherein the water absorption capacity of the HOF is maintained following recycling.

17. The method claim 15, wherein the intercrossed macroporous network structure of the HOF is maintained following recycling.

18. The method of claim 1, wherein the HOF is made by a method comprising:
   dissolving trimesic acid in water at a temperature of 50-80° C. to form a trimesic acid solution;
   dissolving guanazole in water to form a guanazole solution;
   adding dropwise the guanazole solution to the trimesic acid solution at a temperature of 50-80° C. to form a reaction mixture;
   cooling the reaction mixture to 20-40° C. to form a precipitate;
   separating and drying the precipitate at a temperature of 50-80° C. to form the HOF.

* * * * *